(12) United States Patent
Nagao et al.

(10) Patent No.: US 11,231,414 B2
(45) Date of Patent: Jan. 25, 2022

(54) MAGNETIC COMPOSITE PARTICLES, METHOD FOR MANUFACTURING THE SAME, AND IMMUNOASSAY PARTICLES

(71) Applicants: TOHOKU UNIVERSITY, Miyagi (JP); DOWA ELECTRONICS MATERIALS CO., LTD., Tokyo (JP)

(72) Inventors: Daisuke Nagao, Miyagi (JP); Mikio Konno, Miyagi (JP); Haruyuki Ishii, Miyagi (JP); Kumiko Hayashi, Miyagi (JP); Natsuki Kohama, Miyagi (JP); Takayuki Yoshida, Tokyo (JP); Toshihiko Ueyama, Tokyo (JP)

(73) Assignees: TOHOKU UNIVERSITY, Miyagi (JP); DOWA ELECTRONICS MATERIALS CO., LTD., Tokyo (JP)

( * ) Notice: Subject to any disclaimer, the term of this patent is extended or adjusted under 35 U.S.C. 154(b) by 60 days.

(21) Appl. No.: 16/329,579

(22) PCT Filed: Aug. 31, 2017

(86) PCT No.: PCT/JP2017/031323
§ 371 (c)(1),
(2) Date: May 16, 2019

(87) PCT Pub. No.: WO2018/043633
PCT Pub. Date: Mar. 8, 2018

(65) Prior Publication Data
US 2019/0271694 A1 Sep. 5, 2019

(30) Foreign Application Priority Data
Sep. 1, 2016 (JP) .............................. JP2016-171157

(51) Int. Cl.
*G01N 33/531* (2006.01)
*G01N 33/543* (2006.01)
(Continued)

(52) U.S. Cl.
CPC ....... *G01N 33/54333* (2013.01); *C01G 49/08* (2013.01); *G01N 33/531* (2013.01); *G01N 33/543* (2013.01); *G01N 33/553* (2013.01)

(58) Field of Classification Search
CPC .......... G01N 33/54333; G01N 33/553; G01N 33/543; G01N 33/531; G01N 33/5434; C01G 49/08
See application file for complete search history.

(56) References Cited

U.S. PATENT DOCUMENTS

| | | |
|---|---|---|
| 4,554,088 A | 11/1985 | Whitehead et al. |
| 4,873,102 A | 10/1989 | Chang et al. |

(Continued)

FOREIGN PATENT DOCUMENTS

| | | |
|---|---|---|
| JP | 7-6986 | 1/1995 |
| JP | 2000-306718 | 11/2000 |

(Continued)

OTHER PUBLICATIONS

International Search Report in International Patent Application No. PCT/JP2017/031323, dated Nov. 21, 2017.
(Continued)

*Primary Examiner* — Tracy Vivlemore
*Assistant Examiner* — Nam P Nguyen
(74) *Attorney, Agent, or Firm* — Greenblum & Bernstein, P.L.C.

(57) ABSTRACT

To provide magnetic composite particles which can be separated from a sample solution in a short period of time using magnetism, and furthermore, have an excellent dispersion stability in the sample solution, which are magnetic composite particles in which an outer shell is formed on surfaces of core particles containing an inorganic oxide or a polymer, wherein the outer shell comprises magnetic nanoparticles and a silicon compound, the value of the volume (Continued)

average particle diameter (dTEM) of the magnetic composite particles measured by a transmission electron microscope is 30 nm or more to 210 nm or less, and the value of (dDLS)/(dTEM) which is the ratio of the value of the particle diameter (dDLS) of the particles measured by a dynamic light scattering method and the value of the volume average particle diameter (dTEM) is 2.0 or less.

10 Claims, 4 Drawing Sheets

(51) Int. Cl.
  *G01N 33/553* (2006.01)
  *C01G 49/08* (2006.01)

(56) References Cited

U.S. PATENT DOCUMENTS

| | | |
|---|---|---|
| 2004/0115433 A1 | 6/2004 | Elaissari et al. |
| 2006/0188932 A1 | 8/2006 | Oka et al. |
| 2009/0014682 A1 | 1/2009 | Takahashi et al. |
| 2016/0069870 A1 | 3/2016 | Ueya |

FOREIGN PATENT DOCUMENTS

| | | |
|---|---|---|
| JP | 2002-90366 | 3/2002 |
| JP | 2004-533530 | 11/2004 |
| JP | 2005-241547 | 9/2005 |
| JP | 2007-49052 A | 2/2007 |
| JP | 2008-116265 | 5/2008 |
| JP | 2010-132513 | 6/2010 |
| JP | 2010132513 A * | 6/2010 |
| JP | 4873123 | 2/2012 |
| JP | 2012-177691 | 9/2012 |
| JP | 5419199 | 2/2014 |
| JP | 2015-227806 | 12/2015 |
| JP | 2016-57105 | 4/2016 |
| JP | 2016-105066 | 6/2016 |
| WO | 2009/151148 A1 | 12/2009 |
| WO | 2011/096394 | 8/2011 |

OTHER PUBLICATIONS

International Preliminary Report on Patentability in International Patent Application No. PCT/JP2017/031323, dated Mar. 5, 2019.
European Search Report, European Patent Office, Application No. 17846637.1, dated May 26, 2020.
Pich A et al., "Composite magnetic particles: 1. Deposition of magnetite by heterocoagulation method", Polymer, Elsevier Science Publishes B.V, GB, vol. 46, No. 4, Feb. 7, 2005 (Feb. 7, 2005), pp. 1077-1086, XP027728303, ISSN: 0032-3861.
Andrij Pich et al., "Composite Magnetic Particles as Carriers for Laccase from Trametes versicolor", Macromolecular Bioscience, vol. 6, No. 4, Apr. 12, 2006 (Apr. 12, 2006), pp. 301-310, XP055082926, ISSN: 1616-5187, DOI:10.1002/mabi.200500192.
Adler H-J et al., "Magnetorheology of Synthesized Core-Shell Structured Nanoparticle", IEEE Transactions on Magnetics, IEEE Service Center, New York, NY, US, vol. 41, No. 10, Oct. 1, 2005 (Oct. 1, 2005), pp. 3448-3450, XP011140875, ISSN: 0018-9464, DOI: 10.1109/TAMG.2005.855197.
Bizdoaca E L et al., "Self-assembly and magnetism in core-shell microspheres", Journal of Vacuum Science and Technology: Part A, AVS/AIP, Melville, NY., US, vol. 21, No. 4, Jul. 1, 2003 (Jul. 1, 2003), pp. 1515-1518, XP012006468, ISSN: 0734-2101, DOI: 10.1116/1.1564031.

* cited by examiner

MAGNETIC COMPOSITE PARTICLES, METHOD FOR MANUFACTURING THE SAME, AND IMMUNOASSAY PARTICLES

TECHNICAL FIELD

The present invention relates to magnetic composite particles which are suitable for use in an immunoassay, etc., and a method for manufacturing the same, and furthermore, relates to immunoassay particles produced using the magnetic composite particles.

BACKGROUND ART

In order to separate and collect targets such as various proteins, nucleic acids and cells from a sample liquid such as blood, antigen-antibody measurement methods in which an antibody suitable for a respective target substance is carried on the surface of a predetermined particle, and the particle is recovered and analyzed after the capture of the target substance have been investigated.

Recently, in order to shorten the measurement time in applications requiring rapid measurement and analysis in clinical examinations, a method which uses a carrier on which an antibody is carried and provided with a magnetic property for rapidly recovering the magnetic carrier, and recovering a target substance by providing magnetism from the outside after capturing the target substance has been investigated.

In order to impart a high magnetic separation characteristic to a fixed carrier provided with a magnetic property, increasing the proportion of the magnetic component comprised in a magnetic body added to the fixed carrier, and making a magnetic body as one having a high saturation magnetization (specifically, using a magnetic material in which the value of the saturation magnetization is high) is known.

PTL 1 proposed magnetic polymer particles mainly used for immunodiagnosis and the like, wherein the average particle diameter is 0.2 to 4.0 μm, and the residual magnetization is 10 to 35% of the saturation magnetization.

On the one hand, in PTL 2, the present inventors disclosed magnetic-substance-containing particles, wherein the volume average particle diameter is 10 to 500 nm, the CV value of the number average particle diameter is 8% or less, and, the saturation magnetization at 25° C. is 15 emu/g or more obtained by disposing an outer shell layer on the surfaces of core particles containing an inorganic oxide or a polymer as a fixed carrier provided with a magnetic property, and containing magnetite particles and sodium silicate together in the outer shell layer.

CITATION LIST

Patent Literature

[PTL 1] JP-A-2000-306718
[PTL 2] Japanese Patent No. 5419199

SUMMARY OF INVENTION

Technical Problem

The magnetic-substance-containing particles which is the fixed carrier provided with a magnetic property disclosed in PTL 2 exhibit an excellent magnetic separation characteristic.

However, according to further research by the present inventors, it sometimes takes time to separate and recover the magnetic-substance-containing particles from a sample solution in which magnetism is used.

Furthermore, it was discovered that it is important that the magnetic-substance-containing particles also have a high spontaneous sedimentation resistance. Specifically, it was discovered that when the spontaneous sedimentation resistance of the magnetic-substance-containing particles is insufficient, spontaneous sedimentation sometimes occurs in the sample solution in a short period of time, and, therefore, further improvement is required.

When the dispersibility in the sample solution of the magnetic-substance-containing particles is insufficient, the contact between the antigen and the antibody in the sample solution is sometimes insufficient, thus, the capture of the target substance contained in the sample solution is incomplete in some cases. As a result, the presence of an important target substance in the sample solution may be overlooked, possibly leading to a misdiagnosis.

The present invention is made according to the above circumstances, and the problem to be solved is to provide magnetic composite particles which can be separated from a sample solution in a short period of time using magnetism, and furthermore, which are excellent in dispersion stability in the sample solution.

Solution to Problem

The present inventors conducted research to solve the aforementioned problems, and as a result, achieved magnetic composite particles in which an outer shell is formed on surfaces of core particles containing an inorganic oxide or a polymer, wherein the outer shell comprises magnetic nanoparticles and a silicon compound, the value of the volume average particle diameter (dTEM) of the magnetic composite particles measured by a transmission electron microscope is 30 nm or more to 210 nm or less, and the value of (dDLS)/(dTEM) is 2.0 or less which is the ratio of the value of the particle diameter (dDLS) of the particles measured by a dynamic light scattering method and the value of the volume average particle diameter (dTEM).

The magnetic composite particles comprise a predetermined amount of a nano-sized magnetic substance (also referred to as the "magnetic nanoparticles" in the present invention) in the outer shell provided on the surfaces of fine particles (also referred to as the "core particles" in the present invention) containing an inorganic oxide or a polymer. Specifically, a high saturation magnetization is expressed by forming the magnetic nanoparticles with magnetite or γ-iron oxide. Furthermore, the peeling of the magnetic nanoparticles from the magnetic composite particle surface can be suppressed by covering the outer shell of the magnetic composite particle surface with a silicon compound so as to contain the magnetic nanoparticles.

As a result, the magnetic composite particles according to the present invention having the above configuration can be separated from the sample solution in a short period of time using magnetism. Furthermore, it is considered that the dispersion stability in the sample solution is excellent by the magnetic composite particles having a predetermined particle diameter.

Namely, the first invention for solving the aforementioned object is
magnetic composite particles in which an outer shell is formed on surfaces of core particles containing an inorganic oxide or a polymer, wherein the outer shell comprises magnetic nanoparticles and a silicon compound, a value of a volume average particle diameter (dTEM) of the magnetic composite particles measured by a transmission electron microscope is 30 nm or more to 210 nm or less, and the value of (dDLS)/(dTEM) which is a ratio of a value of the particle diameter (dDLS) of the particles measured by a dynamic light scattering method and the value of the volume average particle diameter (dTEM) is 2.0 or less.

The second invention is
the magnetic composite particles according to the first invention, further comprising a silane coupling agent in the outer shell.

The third invention is
the magnetic composite particles according to the first or second invention, wherein the magnetic nanoparticles comprising the outer shell are magnetite or γ-iron oxide.

The fourth invention is
the magnetic composite particles according to any of the first to third inventions having a spherical or a nearly spherical shape.

The fifth invention is
the magnetic composite particles according to any of the first to fourth inventions, wherein a value of a saturation magnetization is 30 $Am^2/kg$ or more to 200 $Am^2/kg$ or less.

The sixth invention is
the magnetic composite particles in which an outer shell is formed on surfaces of core particles containing an inorganic oxide or a polymer, wherein
the outer shell comprises magnetic nanoparticles and a silicon compound,
the value of a volume average particle diameter (dTEM) of the magnetic composite particles measured by a transmission electron microscope is 30 nm or more to 210 nm or less, and the magnetic composite particles can be reversibly controlled to a cluster state or a dispersion state by application or removal of a magnetic field.

The seventh invention is
the magnetic composite particles according to the sixth invention, wherein the cluster state of the magnetic composite particles is a strand-shaped cluster state.

The eighth invention is
the magnetic composite particles according to the seventh invention, wherein a long side length is 0.5 µm or more to 5 µm or less in a strand-shaped cluster state.

The ninth invention is
the magnetic composite particles according to the seventh or eighth invention, wherein
the magnetic composite particles in the strand-shaped cluster state migrate at a speed of 3 µm/s or more to 15 µm/s or less when a magnetic field of 0.1 T or more to 0.4 T or less is applied.

The tenth invention is
immunoassay particles, wherein an antibody is present on the outer shell of the magnetic composite particles according to any one of the first to ninth inventions.

The eleventh invention is
a method for manufacturing the magnetic composite particles comprising:
producing a suspension of magnetic nanoparticles;
producing core particles comprising an inorganic oxide or a polymer, and having a value of a volume average particle diameter measured from a transmission electron microscope image of 20 nm or more to 200 nm or less,
adding the core particles to the suspension of the magnetic nanoparticles and producing a suspension of heteroaggregation particles, and adding an aqueous solution of a silicon compound to the suspension of the heteroaggregation particles, thereby providing a layer of the silicon compound on the surfaces of the heteroaggregation particles, and producing a suspension of the magnetic composite particles in which a value of a volume average particle diameter (dTEM) measured from a transmission electron microscope image is 30 nm or more to 210 nm or less.

Advantageous Effects of Invention

The magnetic composite particles according to the present invention are excellent in dispersion stability in a sample solution, and, can be separated from the sample solution in a short period of time using magnetism.

DESCRIPTION OF EMBODIMENTS

There is a case requiring time to separate and recover the magnetic particles from the sample solution as stated above, or a case when it is necessary to verify whether or not the obtained measurement effect is valid because spontaneous sediment of the magnetic particles occurs. Therefore, there is a problem that the magnetic particles according to the prior art cannot sufficiently respond to applications which require rapid and accurate measurement results.

Under such circumstances, the present inventors conducted research, and solved the aforementioned problem by providing an outer shell comprising magnetic nanoparticles on the surfaces of the core particles comprising an inorganic oxide or a polymer, thereby producing magnetic composite particles having a core-shell structure.

First, the magnetic composite particles according to the present invention will be described with reference to the drawings.

Figure 1:
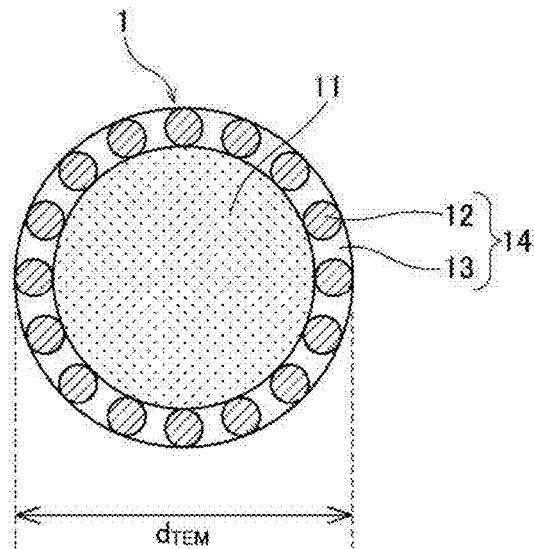
FIG. 1 is a schematic cross-sectional view of magnetic composite particles according to the present invention.

FIG. 1 is a schematic cross-sectional view of the magnetic composite particles according to the present invention.

A magnetic composite particle 1 according to the present invention has a core particle 11 in the center and magnetic nanoparticles 12 are adsorbed on the surface of the core particle 11. Furthermore, the core particle 11 is covered by a layer of a silicon compound 13. Moreover, the layer of the silicon compound 13 comprises the magnetic nanoparticles 12, thereby constituting the outer shell 14.

Here, 1. Magnetic nanoparticles, 2. Core particles, 3. Layer of the silicon compound, 4. Magnetic composite particles, 5. Magnetic composite particles when a magnetic field is applied, and 6. Synthesis of the magnetic composite particles will be explained in order.

1. Magnetic Nanoparticles

The magnetic nanoparticles 12 are formed by magnetite ($Fe_3O_4$) or γ-iron oxide, each having an average particle diameter of preferably 5 nm or more 50 nm or less.

Moreover, a value of a saturation magnetization of the magnetic nanoparticles 12 may be 0.1 $Am^2/kg$ or more to 200 $Am^2/kg$ or less, more preferably 120 $Am^2/kg$ or less, and even more preferably 80 $Am^2/kg$ or less. If the value of the saturation magnetization is 0.1 $Am^2/kg$ or more, a sufficient magnetic field responsiveness can be imparted to the magnetic composite particle 1, and if the value of the saturation magnetization is 200 $Am^2/kg$ or less, it is possible to prevent a situation in which the residual magnetization causes the aggregation of the magnetic composite particle 1.

Further, a carried amount of the magnetic nanoparticles 12 in the magnetic composite particle 1 is preferably 0.095% by mass or more to 95% by mass or less. If the carried amount is 0.095% by mass or more, the magnetic field response speed of the magnetic composite particle 1 can be secured, and if the carried amount is 95% by mass or less, the density of the magnetic composite particle 1 does not become excessive, and therefore, the dispersibility in the sample solution can be secured.

2. Core Particle

The core particle 11 is constituted by an inorganic oxide or a polymer. A volume average particle diameter of the core particles is preferably of 20 nm or more to 200 nm or less. For example, polymethyl methacrylate (also referred to as "PMMA" in the present invention) and polystyrene (also referred to as "PSt" in the present invention) may be provided as the polymer.

Examples of the inorganic oxide include silica, talc, kaolinite, magnesium carbonate, calcium carbonate and the like.

A property of these polymers and inorganic oxides is that the density may be 5.0 $g/cm^3$ or less, preferably 4.0 $g/cm^3$ or less, and more preferably 3.0 $g/cm^3$ or less. Selecting core particles having the density in this range is preferable in that the buoyancy and the weight of the core particle itself are balanced at the time of dispersing in the sample solution, and the dispersibility in the sample solution can improve. However, if the buoyancy is excessive, the core particles may float on the sample solution. From the viewpoint of preventing this situation, the core particles in which the density is 0.3 $g/cm^3$ or more, preferably 0.5 $g/cm^3$ or more may be selected although this is dependent upon the specific gravity of the sample solution to be tested.

However, in the present invention, the particles with magnetic nanoparticles 12 adsorbed and aggregated on the surfaces of the core particles 11 may also be referred to as "heteroaggregation particles".

3. Layer of the Silicon Compound

The layer of a silicon compound 13 is preferably constituted by a polymer of a silicon oxide, for example, tetraethylorthosilicate ($Si(OC_2H_5)_4$) (also referred to as "TEOS" in the present invention). Furthermore, the layer of the silicon compound 13 even more preferably contains a silane coupling agent, for example, 3-methacryloxy propyrtrimethoxysilane (also referred to as "MPTMS" in the present invention), and is polymerized using two or more types of silicon compound raw materials. This is because a polymerizable functional group can be introduced into the molecule, and, a hydroxyl group (—OH) which serves as a standpoint for the antibody can be introduced.

From the above viewpoint, the amount of the silane coupling agent in the layer of the silicon compound 13 is preferably 0.001 $mol/m^3$ or more to 1 $kmol/m^3$ or less, in the case when the concentration of the heteroaggregation particle is 0.01% by volume or more to 1.0% by volume or less.

If the amount of the silane coupling agent is 0.001 $mol/m^3$ or more, the effect as a silane coupling agent is exhibited, and the amount of the silane coupling agent is 1 $kmol/m^3$ or less, the self-condensation of the silane coupling agent molecules can be avoided.

The outer shell 14 which is the layer of the silicon compound 13 containing the magnetic nanoparticles 12 exhibits the effect that the magnetic nanoparticles 12 are prevented from separating from the surfaces of the core particle 11.

4. Magnetic Composite Particles

The magnetic composite particle 1 preferably has a spherical or a nearly spherical shape, but the volume average particle diameter of the particles can be calculated and measured by, for example, a caliper, etc., from the transmission electron microscope image of the magnetic composite particle 1. In the present invention, the volume average particle diameter calculated from the transmission electron microscope image is described as ($d_{TEM}$).

However, the "magnetic composite particle 1 has a spherical or a nearly spherical shape" means that the cross section of the magnetic composite particle is circular or approximately circular, and the aspect ratio in the cross section is, for example, 1.3 or less.

The magnetic composite particle 1 according to the present invention preferably has a value of saturation magnetization of 30 $Am^2/kg$ or more to 200 $Am^2/kg$ or less. This is because if the value of the saturation magnetization is 30 $Am^2/kg$ or more, the magnetic composite particle 1 can be easily separated from the sample solution in a short period of time using magnetism such as a permanent magnet. On the one hand, if the value of the saturation magnetization is 200 $Am^2/kg$ or less, it is possible to prevent a situation such as the aggregation of the magnetic composite particles caused by the residual magnetization.

Figure 2:
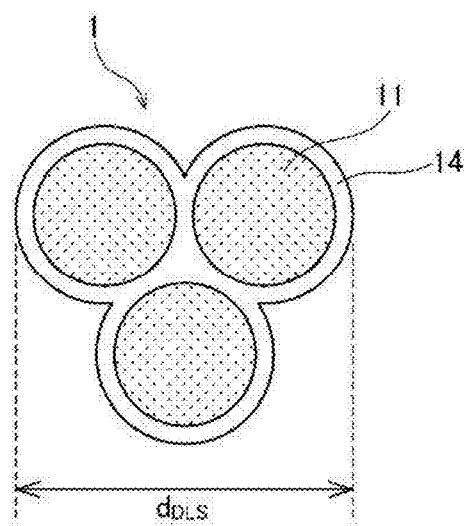
FIG. 2 is a schematic cross-sectional view of the magnetic composite particles according to the present invention which are aggregated in a sample solution.

FIG. 2 is a schematic cross-sectional view of the magnetic composite particle 1 according to the present invention aggregated in the sample solution.

While there are cases when the magnetic composite particle 1 according to the present invention may be dispersed singly in the sample solution, there are also cases when two or more particles are aggregated. FIG. 2 is a schematic cross-sectional view of a state in which three magnetic composite particle 1 are aggregated.

The particle diameter of the magnetic composite particle 1 aggregated in the sample solution can be measured and calculated by, for example, a dynamic light scattering method. In the present invention, the particle diameter calculated by the dynamic light scattering method is described as ($d_{DLS}$). However, the ($d_{DLS}$) can also be considered as a hydrodynamic diameter.

The ($d_{TEM}$) of the magnetic composite particle 1 is 30 nm or more to 210 nm or less, and the value of ($d_{DLS}$)/($d_{TEM}$) which is the ratio of ($d_{DLS}$) and ($d_{TEM}$) is 2 or less.

When the value of ($d_{DLS}$)/($d_{TEM}$) is 2 or less, it indicates that the particle diameter in one particle in the sample solution is almost the same as an original volume average particle diameter, or that they are remarkably close. Namely, the magnetic composite particles are present as in the sample solution ensuring a nearly monodisperse form without being aggregated. Therefore, the magnetic composite particle 1 can have excellent dispersion stability in the sample solution.

An immunoassay particle having a good responsiveness in a magnetic field can be obtained in the sample solution by adsorbing the desired antibody on the magnetic composite particles according to the present invention as described above. As a result, it is considered that it becomes possible to capture all of the antigen present in the sample solution, and it is considered that the risk of a misdiagnosis can be reduced.

5. Magnetic Composite Particles when a Magnetic Field is Applied

When a magnetic field is applied (ON) to the magnetic composite particles according to the present invention dispersed in a predetermined solvent, each magnetic composite particle aggregates to form a cluster state in a magnetic field direction. Moreover, when the magnetic field is removed (OFF), the cluster state collapses, and the magnetic composite particles return to a nearly monodisperse state. Namely, the magnetic composite particles according to the present invention are magnetic composite particles which can be reversibly controlled to a cluster state or a dispersion state by the application or the removal of the magnetic field.

Moreover, it was discovered that the cluster state is a strand-shaped cluster state (also referred to as the "cluster strand" in the present invention) in the magnetic field direction.

On the one hand, if a magnetic field is applied, the strand-shaped or a globular cluster state is also formed in the magnetic composite particles according to the prior art. However, the strand-shaped or the globular cluster state is maintained even if the magnetic field is removed.

The magnetic composite particles according to the present invention can be reversibly controlled in a cluster strand state or a dispersion state. Utilizing this characteristic, for example, the particles can be easily separated by making to the cluster strand state during the magnetic separation operation, and can be made to the dispersion state when the magnetic field is removed. Namely, a target component in a predetermined liquid to be tested can be recovered at a high yield, and it is preferable that the recovery of the magnetic composite particles from the liquid to be tested is performed rapidly.

In other words, it is possible to recover the magnetic composite particles generated in the liquid without loss even at the manufacturing stage, thus, the yield improves, and a highly dispersed reagent can be obtained at the time of use. As for the efficacy at the time of use of the magnetic composite particles, the particles are uniformly dispersed in the liquid in the absence of a magnetic field, thus, making it possible to reduce the unintentional dropout of the target component present in the liquid to be tested. Further, after recovering the target component by acting on the sample solution, the magnetic particles including the target component can be recovered together, and this contributes to a rapid and reliable judgement.

It is considered that the difference in the behaviors between the magnetic composite particles according to the present invention and the magnetic composite particles according to the prior art by the application or the removal of the magnetic field, is caused by the difference in the particle diameter. Namely, it is considered that the magnetic composite particle according to the present invention has a smaller particle diameter compared to the particles according to the prior art, thus, Brownian motion is largely influenced, and the cluster state collapses due to the removal of the magnetic field. As a result, it is considered that the magnetic composite particles according to the present invention are magnetic composite particles which can be reversibly controlled to a cluster state or a dispersion state by the application or the removal of a magnetic field.

Since the magnetic composite particle according to the present invention has a small particle diameter, the movement speed is low when dispersed in a predetermined solvent. As a result, for example, there was concern that a long period of time is required to recover the magnetic composite particles. However, the magnetic composite particles can be in a cluster strand by the application of the magnetic field as described above, thus, it is possible to obtain the effect in which the magnetophoretic movement speed becomes fast.

As a specific example of the magnetophoretic movement, the magnetic composite particles in the cluster strand state migrate at a moving speed of 3 μm/s or more to 15 μm/s or less when a magnetic field of 0.1 T or more to 0.4 T or less was applied.

6. Synthesis of the Magnetic Composite Particles

The synthesis of the magnetic composite particles according to the present invention will be described in order of 1) Synthesis of the magnetic nanoparticles, 2) Synthesis of the core particles, 3) Synthesis of the heteroaggregation particles, and 4) Synthesis of the magnetic composite particles.

1) Synthesis of the Magnetic Nanoparticles

The magnetic nanoparticles which are the magnetic particles are generally synthesized by a method called the co-precipitation method. This technique is a synthesis method for producing magnetic nanoparticles of magnetite by only adding a basic solution to a mixed solution containing $Fe^{2+}$ and $Fe^{3+}$ at a ratio of 1:2. On the one hand, γ-iron oxide (maghemite) is obtained by, for example, by drying magnetite in the air atmosphere, the magnetite being obtained by the aforementioned method, followed by heating and oxidizing at at a low temperature (about 350° C.).

It is preferable to perform a surface treatment by adding a coupling agent in order to impart a positive charge to the surfaces of the produced magnetic nanoparticles and create a stabilized dispersion.

However, the crystal structure of the substances constituting the magnetic nanoparticles can be identified, for example, by applying the aforementioned liquid on a preparation and allowing it to dry naturally, and then analyzing using X-ray diffraction.

2) Synthesis of the Core Particles

Potassium persulfate and ammonium persulfate can be added to a mixture of St monomer and MMA monomer and polymerized, to produce polymerized particles as the material of the core particles having a volume average particle diameter of about 50 nm.

Further, the polymerized particles of PMMA can be produced by soap-free emulsion polymerization using a MMA monomer as the material of the core particles having a volume average particle diameter of about 100 nm.

Furthermore, for the purposes of increasing the affinity of the magnetic nanoparticles to the surfaces of the obtained polymerized particles, and, introducing a functional group which can serve as an origin of the reaction, a polymerizable silane coupling agent MPTMS was added and copolymerized after the start of polymerization to obtain the core particles having a volume average particle diameter from about 50 nm to about 100 nm.

3) Synthesis of the Heteroaggregation Particles

The heteroaggregation particles are obtained by mixing the magnetic nanoparticles with the core particles while shaking and stirring.

4) Synthesis of the Magnetic Composite Particles

The synthesis of the magnetic composite particles was performed by collecting the heteroaggregation particles from the dispersion liquid of the heteroaggregation particles, mixing with the silicon compound liquid, while shaking and stirring.

EXAMPLES

The present invention will be further described below with reference to examples. However, the present invention is not limited by the examples.

Example 1

In Example 1, magnetic composite particles containing the polymer particles having a volume average particle diameter of 47 nm was made as the core particles, $Fe_3O_4$ nanoparticles as the magnetic nanoparticles on the outer shell formed on the surface, and TEOS and MPTMS as the silicon compounds was synthesized and the characteristics were evaluated.

Below, the magnetic composite particles according to Example 1 will be explained in the order of 1. Synthesis of the magnetic nanoparticles, 2. Synthesis of the core particles, 3. Synthesis of the heteroaggregation particles, 4. Synthesis of the magnetic composite particles, and 5. Characteristic evaluation of the magnetic composite particles.
1. Synthesis of the Magnetic Nanoparticles The synthesis of the magnetic nanoparticles according to Example 1 of the present invention will be explained in the order of 1) Raw materials of the magnetic nanoparticles and 2) Synthesis of the magnetic nanoparticles.
1) Raw Materials of the Magnetic Nanoparticles $FeCl_2$ (manufactured by Kojundo Chemical Laboratory Ltd., purity of 99.9%) was prepared as one Fe source of the $Fe_3O_4$ nanoparticles which were the magnetic nanoparticles according to Example 1. Further, $FeCl_3$ (manufactured by Wako Pure Chemical Industries, Ltd.) was prepared as another Fe source.

Moreover, N-trimethoxysilylpropyl-N, N, N,-trimethylammonium chloride (manufactured by GELEST Inc., 50% methanol solution) (also referred to as "TSA" in the present invention) was prepared as the dispersion stabilizer of the magnetic nanoparticles and the coupling agent for imparting the positive charge.

Further, an ammonia solution (manufactured by Wako Pure Chemical Industries, Ltd., special grade reagent 28% by mass aqueous solution) was prepared as a pH adjuster when synthesizing the magnetic nanoparticles.

Furthermore, deionized water having an electric resistance value of 18.2 MΩcm was prepared as a reaction solvent when synthesizing the magnetic nanoparticles.
2) Synthesis of the Magnetic Nanoparticles A separable flask having an inner diameter of 7.5 cm and a height of 15 cm was used as the reaction vessel. A 4-blade pitch paddle having a blade diameter of 5 cm and an inclination angle of 45° was used as a stirrer, and a stirring speed was set to 300 rpm.

186 $cm^3$ of deionized water which had the dissolved oxygen removed by nitrogen bubbling was introduced into the reaction vessel, 5 $cm^3$ of a 2 $kmol/m^3$ $FeCl_2$ aqueous solution and 20 $cm^3$ of a 1 $kmol/m^3$ $FeCl_3$ aqueous solution were added, and stirring was initiated at 35° C. Nitrogen was filled in the reaction vessel, and nitrogen bubbling was carried out for 30 minutes.

11.7 $cm^3$ of ammonia solution was introduced into the reaction vessel and the reaction was initiated. 2.1 $cm^3$ of TSA was introduced 30 seconds after the initiation of the reaction, the reaction vessel was stirred continuously for three hours, and the surface treatment of the produced magnetic nanoparticles was performed.

After ethanol at 2 times the weight relative to the predetermined amount of a suspension of the obtained magnetic nanoparticles was added and sufficiently mixed, followed by centrifugation (12000 rpm, 15 minutes) and removal of the supernatant liquid, deionized water was added, and a suspension having a magnetic nanoparticle concentration of 1.0% by mass according to Example 1 was obtained. The volume average particle diameter of the obtained magnetic nanoparticles in the suspension was 8 nm. Further, the saturation magnetization of the magnetic nanoparticles was 58 emu/g.
2. Synthesis of the Core Particles The synthesis of the core particles according to Example 1 of the present invention will be explained in the order of 1) Raw materials of the core particles and 2) Synthesis of the core particles.
1) Raw Materials of the Core Particles Styrene (St) (manufactured by Wako Pure Chemical Industries, Ltd., special grade reagent, purity of 99%), and methyl methacrylate (MMA) (manufactured by Wako Pure Chemical Industries, Ltd., special grade reagent, purity of 98%) were prepared as the monomer for forming the core particle according to Example 1.

Further, sodium octadecyl sulfate (SOS) (Ward Hill, Mass., USA) was prepared as an anionic surfactant.

In this case, in order to remove the hydroquinone of the polymerization inhibitor contained in the St and MMA, the St and MMA were passed through a glass column filled with a polymerization inhibitor remover (manufactured by Sigma-Aldrich Co).

Ammonium persulfate (APS) (manufactured by Wako Pure Chemical Industries, Ltd., special grade reagent, purity of 98%) was prepared as the polymerization initiator at the time of the core particle synthesis according to Example 1.

3-methacryloxy proprytrimethoxysilane (MPTMS) (manufactured by Shin-Etsu Chemical Co., Ltd., special grade reagent, purity of 95%) was prepared as the polymerizable silane coupling agent at the time of the core particle synthesis according to Example 1.
2) Synthesis of the Core Particles A cylindrical sealed glass reactor having an internal volume of 500 $cm^3$ and an inner diameter of 7.5 cm was used for the reaction, and a 4-blade paddle was used for stirring.

First, a deionized aqueous solution of SOS was introduced to the reactor and nitrogen bubbling was performed for 30 minutes, and then, the bubbling was switched to a nitrogen flow. St and a monomer of MMA were added, stirred for 20 minutes, then, APS was added to initiate polymerization. The stirring speed was set to 360 rpm. The polymerization reaction was performed at 70° C. for 6 hours while continuously stirring to obtain a suspension containing the core particles. At this time, 1.40 g of MPTMS was added 40 minutes after initiating the polymerization.

At this time, the reaction volume of the polymerization reaction was 250 g of pure water, 3.9 g of St, 3.75 g of MMA, 0.0373 g of SOS, and 1.14 g of APS.

After the termination of the polymerization reaction, the obtained suspension was centrifuged (12000 rpm, 15 minutes), and the supernatant was removed to collect the core particles, the core particles were again dispersed by ultrasonic irradiation into the deionized water and washed by centrifugation. The washing by centrifugation was carried out three times, and the core particles according to Example 1 were dispersed in the deionized water. The volume average particle diameter of the obtained core particles was 47 nm.

3. Synthesis of the Heteroaggregation Particles

The core particles synthesized in "2. Synthesis of the core particles" and the suspension of the magnetic nanoparticles according to Example 1 synthesized in "1. Synthesis of the magnetic nanoparticles" were added to a centrifuge tube having a volume of 50 cm$^3$, shaken and stirred for 1 minute to synthesize the heteroaggregation particles.

At this time, the volume of the suspension was 20 cm$^3$, the core particles were 0.069% by volume, and the magnetic nanoparticles were 0.058% by volume.

The suspension containing the heteroaggregation particles was centrifuged at 12000 rpm for 10 minutes, and the supernatant and the suspended particles were removed. The washing of the heteroaggregation particles by centrifugation was carried out three times, and a suspension of the heteroaggregation particles according to Example 1 was obtained.

4. Synthesis of the Magnetic Composite Particles

The obtained suspension of the heteroaggregation particles according to Example 1 was centrifuged and the heteroaggregation particles were collected, water was added thereto, and ultrasonic dispersion was performed for 1.5 hours to obtain the suspension. Ethanol, 0.41 cm$^3$ of 28% ammonia solution, TEOS, and MPTMS were added in order thereto, shaken and stirred at room temperature for 24 hours, and a silicon compound layer was provided on the heteroaggregation particles.

At this time, the heteroaggregation particles were 0.12% by volume, TEOS was 10 mol/m$^3$, MPTMS was 10 mol/m$^3$, water was 3 to 13 kmol/m$^3$, and ammonia was 0.3 mol/m$^3$, and the volume of the reaction liquid was 20 cm$^3$.

The obtained suspension was centrifuged at 12000 rpm for 10 minutes, the precipitate was collected and again dispersed in water to obtain the suspension of the magnetic composite particles according to Example 1.

5. Evaluation of the Characteristics of the Magnetic Composite Particles

Regarding the obtained magnetic composite particles according to Example 1, the volume average particle diameter ($d_{TEM}$) of the magnetic composite particles was measured by TEM, the ($d_{DLS}$) of the magnetic composite particles was measured by a dynamic light scattering photometer, and the dispersibility was confirmed.
Moreover, the saturation magnetization was measured as the magnetic characteristic of the magnetic composite particles, and the results are described in Table 1.

However, each measurement method will be explained below.

1) Measurement of the Volume Average Particle Diameter ($d_{TEM}$) by TEM

Several drops of the suspension of the magnetic composite particles which were the generated particles according to Example 1 were expanded on respective mesh adhered with a collodion membrane (manufactured by JEOL Ltd., 200 mesh), and were sufficiently dried to obtain the measurement sample.

The measurement sample was loaded into a STEM device (manufactured by Hitachi Ltd., HD-2700), and the volume average particle diameter of the magnetic composite particles was directly measured from the obtained TEM image using calipers (manufactured by Mitutoyo Corporation).

Specifically, the particle diameter of about 200 particles were measured per sample, the volume average particle diameter was obtained by Formula 1, and thus obtained the volume average particle diameter was described as ($d_{TEM}$) of the magnetic composite particles obtained from the TEM image.

Note that, the volume average particle diameters of the magnetic nanoparticles and the core particles can be measured by the same method as the volume average particle diameter of the magnetic composite particles.

$$d_{TEM} = \left( \sum_i n_i d_i^3 / \sum_i n_i \right)^{1/3} \quad \text{(Formula 1)}$$

2) Measurement of the ($d_{DLS}$) of the Magnetic Composite Particles

The ($d_{DLS}$) measurement of the magnetic composite particles in the suspension of the magnetic composite particles according to Example 1 was performed by the dynamic light scattering photometer.

Specifically, the suspension of the magnetic composite particles according to Example 1 was diluted and the concentration of the magnetic composite particles was adjusted to 0.001% by volume to obtain the suspension sample for measuring the ($d_{DLS}$), a sample which was irradiated for 100 minutes with ultrasonic waves was loaded into the dynamic light scattering photometer (manufactured by Otsuka Electronics Co., Ltd., ELSZ-2), and the ($d_{DLS}$) was measured.

3) Method for Verifying the Dispersibility

The suspension sample for measuring the ($d_{DLS}$) was left standing for one day, and verified visually.

When the magnetic composite particles showed a high dispersibility, the suspension state was maintained without being changed. This dispersibility was evaluated as "High". The magnetic composite particles according to Example 1 had a "High" dispersibility.

On the one hand, when the dispersibility could not be sufficiently maintained, a supernatant (transparent layer) was produced on the upper part of the suspension. This dispersibility was evaluated as "Medium".

Furthermore, when the dispersibility could not be maintained, a dark brown solid component settled under the vessel. This dispersibility was evaluated as "Low".

On the one hand, the case of comparing and verifying the dispersibility of a plurality of suspension samples can be carried out by comparing the thickness of the transparent layer which is the supernatant on the upper part of the suspension.

4) Measurement of the Saturation Magnetization ($\sigma s$)

The suspension sample of the magnetic composite particles according to Example 1 was vacuum-dried for 12 hours or more to obtain a powder sample. 2 mg of the powder sample was charged in a vibrating sample magnetometer (VSM, manufactured by Toei Scientific Industrial Co., Ltd., PV-M20-5). Moreover, the measurement range was set to −10000 to +10000 Oe, and the arithmetic mean of the absolute value of the magnetization of the magnetic composite particles according to Example 1 at −10000 Oe and +10000 Oe was determined to be the saturation magnetization.

The above results are described in Table 1.

Example 2

In Example 2, the polymer particles having a volume average particle diameter of 106 nm were made as the core particles, and, the heteroaggregation particles having the Fe$_3$O$_4$ nanoparticle as the magnetic nanoparticle on the surface were obtained in the same manner as Example 1, and furthermore, the magnetic composite particles containing TEOS and MPTMS as the silicon compound layers were synthesized, and the characteristics were evaluated.

Below, the magnetic composite particles according to Example 2 will be explained in order of 1. Synthesis of the magnetic nanoparticles, 2. Synthesis of the core particles, 3. Synthesis of the heteroaggregation particles, 4. Synthesis of the magnetic composite particles, and 5. Characteristic evaluation of the magnetic composite particles.

1. Synthesis of the Magnetic Nanoparticles

This synthesis is the same as the synthesis of the magnetic nanoparticles according to Example 1 of the present application.

2. Synthesis of the Core Particles

The synthesis of the core particles according to Example 2 of the present invention will be explained in the order of 1) Raw materials of the core particles and 2) Synthesis of the core particles.

1) Raw Materials of the Core Particles

Methyl methacrylate (MMA) (manufactured by Wako Pure Chemical Industries, Ltd., special grade reagent, purity of 98%) was prepared as one monomer for forming the core particles according to Example 2. In this case, in order to remove the hydroquinone of the polymerization inhibitor contained in the MMA, the MMA was passed through a glass column filled with a polymerization inhibitor remover (manufactured by Sigma-Aldrich Co).

Sodium p-styrenesulfonate (NaSS) (manufactured by Wako Pure Chemical Industries, Ltd., special grade reagent, purity 80%) was prepared as one ionic co-monomer for forming the core particles according to Example 2.

Potassium persulfate (KPS) (manufactured by Wako Pure Chemical Industries, Ltd., special grade reagent, purity of 95%) was prepared as the polymerization initiator at the time of the core particle synthesis according to Example 2.

3-methacryloxy proprytrimethoxysilane (MPTMS) (manufactured by Shin-Etsu Chemical Co., Ltd., special grade reagent, purity of 95%) was prepared as the polymerizable silane coupling agent at the time of the synthesis of the core particle according to Example 2.

Deionized water was prepared in the same manner as in the aforementioned Example 1 as the reaction solvent at the time of the synthesis of the core particle according to Example 2.

2) Synthesis of the Core Particles

A cylindrical sealed glass reactor having an internal volume of 110 cm$^3$ was used for the reaction, and the stirring was performed by a magnetic stirrer.

First, after deionized water was introduced to the reactor and nitrogen bubbling was performed for 30 minutes, and then, the bubbling was switched to a nitrogen flow. MMA and NaSS were added, stirred for 20 minutes, then, KPS was added to initiate the polymerization. The polymerization reaction was performed at 65° C. for 2 hours while continuously stirring to obtain the suspension containing the core particles. At this time, MPTMS was added 40 minutes after the initiation of polymerization.

At this time, the reaction volume of the polymerization reaction was 30 cm$^3$, the concentration of MMA was 200 mol/m$^3$, the concentration of NaSS was 1.0 mol/m$^3$, the concentration of MPTMS was 6.4 mol/m$^3$, and the concentration of KPS was 4.0 mol/m$^3$.

After the termination of the polymerization reaction, the obtained suspension was centrifuged (12000 rpm, 15 minutes), the supernatant was removed to collect the core particles, and the core particles were again dispersed by ultrasonic irradiation into the deionized water and washed by centrifugation. The washing by centrifugation was carried out three times, and the core particles according to Example 2 were dispersed in the deionized water.

3. Synthesis of the Heteroaggregation Particles

The synthesis of the heteroaggregation particles according to Example 2 of the present invention was carried out by the same operation as the synthesis of the heteroaggregation particles according to Example 1 with the exception that the core particles according to Example 2 were used as the core particles.

Moreover, a suspension of the heteroaggregation particles according to Example 2 was obtained.

At this time, the volume of the suspension was 20 cm$^3$, the core particles were 0.094% by volume, and the magnetic nanoparticles were 0.029% by volume.

4. Synthesis of the Magnetic Composite Particles

The magnetic composite particles according to Example 2 were synthesized by performing the same operation as in Example 1 with the exception that the obtained suspension of the heteroaggregation particles according to Example 2 was used.

At this time, the heteroaggregation particles were 0.12% by volume, TEOS was 5 mol/m$^3$, MPTMS was 5 mol/m$^3$, water was 3 to 13 kmol/m$^3$, and ammonia was 0.3 mol/m$^3$, and the volume of the reaction liquid was 20 cm$^3$.

5. Characteristic Evaluation of the Magnetic Composite Particles

Regarding the obtained magnetic composite particles according to Example 2, the particle diameter of the magnetic composite particles was measured by TEM, the ($d_{DLS}$) of the magnetic composite particles were measured by the dynamic light scattering photometer, and the dispersibility was confirmed by the same operations as in Example 1. Moreover, the saturation magnetization was measured as the magnetic property of the magnetic composite particles.

The above results are described in Table 1.

Example 3

The operation when applying or removing a magnetic field using the electromagnetic field device in the obtained magnetic composite particles according to Example 1 will be explained.

Figure 3:
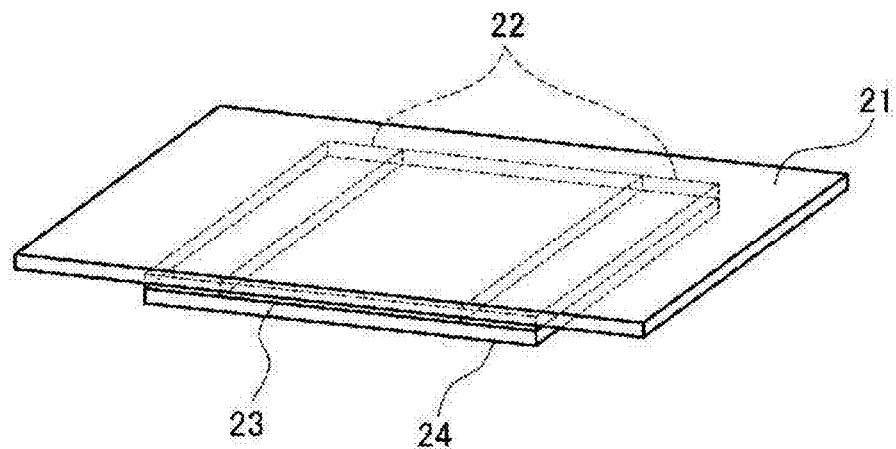
FIG. 3 is a schematic perspective view of a device for applying a magnetic field.
Figure 4:
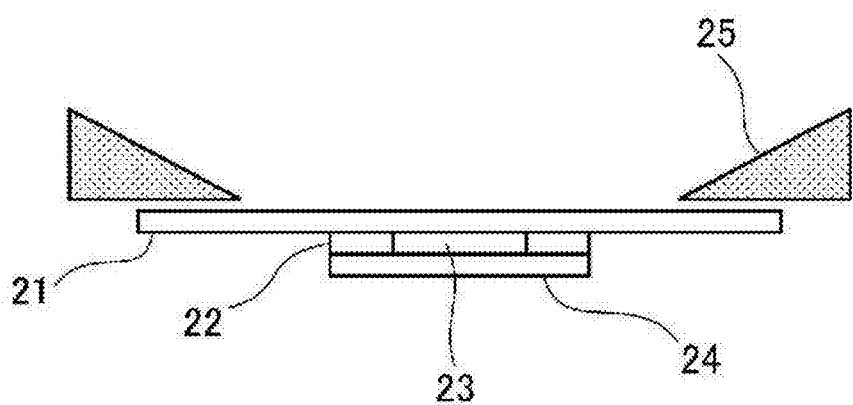
FIG. 4 is a schematic cross-sectional view of a device for applying a magnetic field.

However, FIG. 3 is a schematic perspective view of the electromagnetic field device for applying the magnetic field used in the present example, and FIG. 4 is a schematic cross-sectional view.

Water was selected as the solvent, 1 μl of the suspension (10% by mass) of the magnetic composite particles obtained in Example 1 was added to 1 ml of water and dispersed to obtain 0.01% by mass of a dispersion liquid. The dispersion liquid 23 was sealed between the glass slide 21 and the cover glass 24 of the electromagnetic field device shown in FIGS. 3 and 4. The liquid temperature was made to room temperature (25° C.). However, a spacer 22 was arranged between the glass slide 21 and the cover glass 24, and the glass slide 21 and the cover glass 24 were subjected to a hydophilization treatment by BSA (bovine serum albumin).

Figure 5:
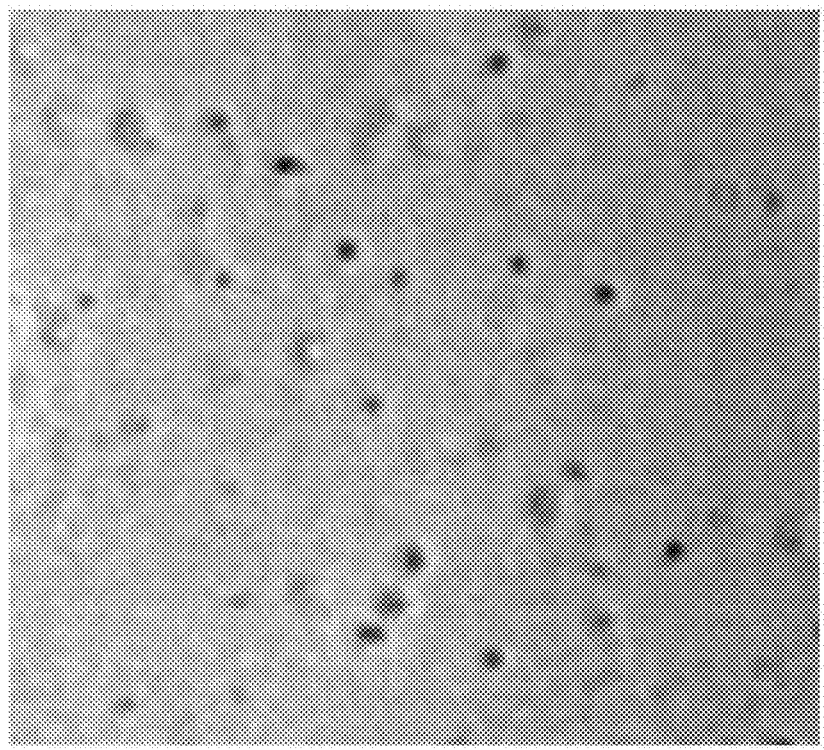
FIG. 5 is a photomicrograph when a magnetic field is removed from the magnetic composite particles.

The microscope image of the magnetic composite particles in the dispersion liquid is shown in FIG. 5.

Next, a current was flown to the electromagnet 25 of the electromagnetic field device, and a magnetic field of 0.38 T was applied to the dispersion liquid.

Figure 6:
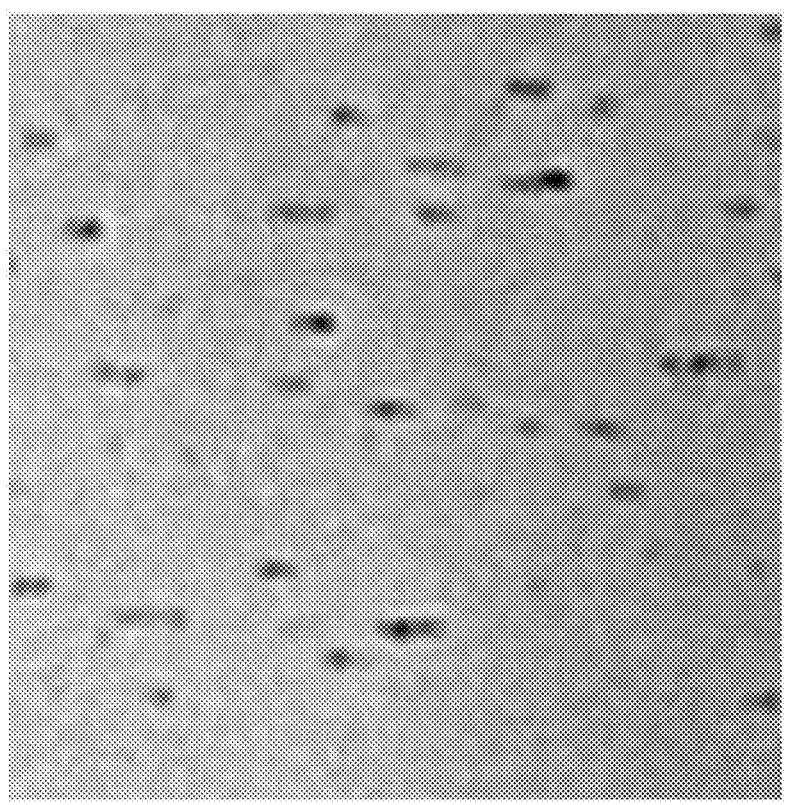
FIG. 6 is a photomicrograph when a magnetic field is applied to the magnetic composite particles.

At this time, the electrophoretic state of the magnetic composite particles according to Example 1 was observed with an optical microscope, and a microscope image of the magnetic composite particles in the dispersion liquid 23 is shown in FIG. 6. Moreover, the cluster strand length formed by the magnetic composite particles and the electrophoretic speed were measured. The cluster strand length formed by the magnetic composite particles was calculated from the microscope image. On the one hand, the electrophoretic speed was measured by tracking a predetermined magnetic composite particle with tracking software (NISA Object Tracking, manufactured by Nikon Corporation).

As a result, when a magnetic field was applied to the dispersion liquid 23, the length of the cluster strand of the long side formed by the magnetic composite particles was 0.5 to 5 μm. Moreover, it was discovered that the electrophoretic speed of the cluster strand formed by the magnetic composite particles tends to correlate with the cluster strand length of the long side, and the longer the cluster strand length, the greater the tendency that the electrophoretic speed increases.

Specifically, the condition that the cluster strand length of the long side exceeds 2 μm showed an electrophoretic speed (approximately, 9 μm/s) equivalent to the commercially available magnetic composite particles according to Comparative example 4 described later.

After measuring the above-stated electrophoretic speed, the cluster strand collapsed when the magnetic field was removed, and the magnetic composite particles returned to a nearly monodisperse dispersion state.

Comparative Example 1

The magnetic composite particles according to Comparative example 1 comprising a polymer particle having a volume average particle diameter of 217 nm as the core particles, $Fe_3O_4$ nanoparticles as the magnetic nanoparticles on the outer shell formed on the surfaces, and TEOS and MPTMS as the silicon oxide were synthesized in the same manner in Example 1, and the characteristics were evaluated.

Regarding the magnetic composite particles according to Comparative example 1, the characteristic evaluation of 1. Synthesis of the magnetic nanoparticles, 2. Synthesis of the core particles, 3. Synthesis of the heteroaggregation particles, 4. Synthesis of the magnetic composite particles, and 5. Magnetic composite particles was performed in the same manner as in Example 2, excluding "2) Synthesis of the core particles in 2. Synthesis of the core particles".

Regarding "2) Synthesis of the core particles in 2. Synthesis of the core particles" according to Comparative example 1, the raw material to be used is the same as in the examples. Moreover, the synthesis conditions of the core particles was suitably adjusted to obtain core particles having a diameter of 217 nm.

Moreover, regarding the obtained magnetic composite particles according to Comparative example 1, the operation was performed in the same manner as in Example 1, the volume average particle diameter ($d_{TEM}$) of the magnetic composite particles was measured by TEM, the ($d_{DLS}$) of the magnetic composite particles was measured by the dynamic light scattering photometer, and the dispersibility was confirmed. Moreover, the saturation magnetization was measured as the magnetic property of the magnetic composite particles.

The above results are described in Table 1.

Comparative Example 2

The "4. Synthesis of the magnetic composite particles" was carried out in the same manner in Example 1 with the exception that 1 μl of a 10 mg/ml particle suspension of the commercially available magnetic composite particles (Name: Sera-Mag Magnetic Streptavidin-coated) was added to 1 ml of water, and only a 30 mol/m³ TEOS was added in place of adding a 10 mol/m³ TEOS and a 10 mol/m³ MPTMS to synthesize the magnetic composite particles according to Comparative example 2, and the characteristics thereof were evaluated. Moreover, the saturation magnetization was measured as the magnetic property of the magnetic composite particles.

The above results are described in Table 1.

Comparative Example 3

The "4. Synthesis of the magnetic composite particles" was carried out in the same manner in Example 2 with the exception that only a 15 mol/m³ TEOS was added in place of adding a 5 mol/m³ TEOS and a 5 mol/m³ MPTMS to synthesize the magnetic composite particles according to Comparative example 3, and the characteristics thereof were evaluated. Moreover, the saturation magnetization was measured as the magnetic property of the magnetic composite particles.

The above results are described in Table 1.

Comparative Example 4

The same operation was performed in Example 3 with the exception that the magnetic composite particles obtained in Example 1 was substituted to the commercially available magnetic composite particles ($d_{TEM}$ 740 nm).

Therefore, the commercially available magnetic composite particles formed the cluster strands by the application of the magnetic field, and showed an electrophoretic speed of 9 μm/s.

Moreover, even if the magnetic field was removed after measuring the electrophoretic speed, the cluster strand was maintained, and the magnetic composite particles did not return to a nearly monodisperse dispersion state.

TABLE 1

|  | Ex. 1 | Ex. 2 | Comp. ex. 1 | Comp ex. 2 | Comp ex. 3 |
|---|---|---|---|---|---|
| Core particle diameter (nm) | 47 | 106 | 217 | 47 | 106 |
| Silicon compound layer | TEOS + MPTMS | TEOS + MPTMS | TEOS + MPTMS | TEOS only | TEOS only |
| $d_{TEM}$ (nm) | 63 | 112 | 226 | 72 | 144 |
| dDLS (nm) | 114 | 200 | 330 | 1130 | 540 |
| (dDLS)/(dTEM) | 1.81 | 1.79 | 1.46 | 15.7 | 3.75 |
| Dispersibility | High | High | High | Low | Low |
| σs(Am²/kg) | 44 | 37 | 14 | 24 | 31 |

LIST OF REFERENCE SIGNS 1. magnetic composite particle
11. core particle
12. magnetic nanoparticle
13. layer of silicon compound
14. outer shell
21. glass slide
22. spacer
23. dispersion liquid
24. cover glass
25. electromagnet

The invention claimed is:

1. Magnetic composite particles in which an outer shell is formed on surfaces of core particles containing an inorganic oxide or a polymer, wherein
the outer shell comprises magnetic nanoparticles and a layer of a silicon compound,
a value of a volume average particle diameter (dTEM) of the magnetic composite particles measured by a transmission electron microscope is 30 nm or more to 210 nm or less,
the value of (dDLS)/(dTEM) which is a ratio of a value of the particle diameter (dDLS) of the particles measured by a dynamic light scattering method and the value of the volume average particle diameter (dTEM) is 2.0 or less,
wherein the magnetic nanoparticles comprising the outer shell are magnetite or γ-iron oxide,
wherein the layer of the silicon compound comprises tetraethylorthosilicate (TEOS) and a silane coupling agent, wherein the silane coupling agent is 3-methacryloxy propyltrimethoxysilane (MPTMS),
wherein the particle diameter (dTEM) is the particle diameter of a single magnetic composite particle, and
wherein the particle diameter (dDLS) is the particle diameter as an aggregate of aggregated magnetic composite particles.

2. The magnetic composite particles according to claim 1 further comprising a silane coupling agent in the outer shell.

3. The magnetic composite particles according to claim 1 having a spherical or a nearly spherical shape.

4. The magnetic composite particles according to claim 1, wherein a value of a saturation magnetization is 30 Am$^2$/kg or more to 200 Am$^2$/kg or less.

5. Magnetic composite particles in which an outer shell is formed on the surfaces of the core particles containing an inorganic oxide or a polymer,
wherein the outer shell comprises magnetic nanoparticles and a layer of a silicon compound,
wherein the value of a volume average particle diameter (dTEM) of the magnetic composite particles measured by a transmission electron microscope is 30 nm or more to 210 nm or less, and the magnetic composite particles can be reversibly controlled to a cluster state or a dispersion state by application or removal of a magnetic field,
wherein the magnetic composite particles exhibit a saturation magnetization of 30 Am$^2$/kg to 200 Am$^2$/kg, and
wherein the layer of the silicon compound comprises tetraethylorthosilicate (TEOS) and a silane coupling agent, wherein the silane coupling agent is 3-methacryloxy propyltrimethoxysilane (MPTMS).

6. Magnetic composite particles in which an outer shell is formed on the surfaces of the core particles containing an inorganic oxide or a polymer,
wherein the outer shell comprises magnetic nanoparticles and a silicon compound,
wherein the value of a volume average particle diameter (dTEM) of the magnetic composite particles measured by a transmission electron microscope is 30 nm or more to 210 nm or less,
wherein the magnetic composite particles are subjected to a magnetic field,
wherein a cluster state of the magnetic composite particles is a strand-shaped cluster state, and
wherein the silicon compound comprises tetraethylorthosilicate (TEOS) and a silane coupling agent, wherein the silane coupling agent is 3-methacryloxy propyltrimethoxysilane (MPTMS).

7. The magnetic composite particles according to claim 6, wherein a long side length is 0.5 μm or more to 5 μm or less when a strand-shaped cluster state.

8. The magnetic composite particles according to claim 6, wherein the magnetic composite particles in the strand-shaped cluster state migrate at a speed of 3 μm/s or more to 15 μm/s or less when a magnetic field of 0.1 T or more to 0.4 T or less is applied.

9. Immunoassay particles, wherein an antibody is present on the outer shell of the magnetic composite particles according to claim 1.

10. A method for manufacturing the magnetic composite particles comprising:
producing a suspension of magnetic nanoparticles;
producing core particles comprising an inorganic oxide or a polymer, and having a value of a volume average particle diameter measured from a transmission electron microscope image of 20 nm or more to 200 nm or less,
adding the core particles to the suspension of the magnetic nanoparticles and producing a suspension of heteroaggregation particles,
adding an aqueous solution of a silicon compound to the suspension of the heteroaggregation particles, thereby providing a layer of the silicon compound on the surfaces of the heteroaggregation particles, and producing a suspension of the magnetic composite particles in which a value of a volume average particle diameter (dTEM) measured from a transmission electron microscope image is 30 nm or more to 210 nm or less, and
wherein the layer of the silicon compound comprises tetraethylorthosilicate (TEOS) and a silane coupling agent, wherein the silane coupling agent is 3-methacryloxy propyltrimethoxysilane (MPTMS).

* * * * *